(12) United States Patent
Zak (10) Patent No.: US 9,211,311 B2
(45) Date of Patent: Dec. 15, 2015

(54) METHODS FOR THE TREATMENT OF NEURODEGENERATIVE DISORDERS

(76) Inventor: Paul J. Zak, Claremont, CA (US)

( * ) Notice: Subject to any disclaimer, the term of this patent is extended or adjusted under 35 U.S.C. 154(b) by 0 days.

(21) Appl. No.: 13/291,921

(22) Filed: Nov. 8, 2011

(65) Prior Publication Data

US 2012/0114561 A1 May 10, 2012

Related U.S. Application Data

(60) Provisional application No. 61/411,291, filed on Nov. 8, 2010.

(51) Int. Cl.
*A61K 49/00* (2006.01)
*A61K 38/11* (2006.01)

(52) U.S. Cl.
CPC ..................................... *A61K 38/11* (2013.01)

(58) Field of Classification Search
None
See application file for complete search history.

(56) References Cited

PUBLICATIONS

Muller et al., Anxiety and Medical Disorders, Aug. 2005, Current Psychiatry Reports 7(4):245-251.*
Guastella et al., A randomized controlled trial of intranasal oxytocin as an adjunct to exposure therapy for social anxiety disorder, Jul. 2009, Psychoneuroendocrinology 34(6):917-923.*

* cited by examiner

*Primary Examiner* — John Ulm
(74) *Attorney, Agent, or Firm* — Klein, O'Neill & Singh, LLP (57) ABSTRACT

Methods for treating neurodegenerative disorders, including Parkinson's disease, are provided. The methods comprise administrating a therapeutically effective amount of oxytocin or oxytocin analogs to alleviate one or more symptoms of Parkinson's disease. Methods for determining the effectiveness of oxytocin therapy by itself or in addition to one or more adjunctive therapies in alleviating one or more symptoms of Parkinson's disease are also discussed.

5 Claims, 5 Drawing Sheets

Fig. 1

Oxytocin

METHODS FOR THE TREATMENT OF NEURODEGENERATIVE DISORDERS

CROSS REFERENCE TO RELATED APPLICATIONS

This application claims the benefit of the filing date of U.S. Provisional Patent Application No. 61/411,291, filed Nov. 8, 2010, the disclosure of which is incorporated by reference.

BACKGROUND OF THE INVENTION

The present invention relates generally to treatments of neurodegenerative disorders, and more particularly to treatments of Parkinson's disease.

Neurodegenerative disorders are a group of central nervous system disorders characterized by the gradual and progressive loss of neural tissues or nerve cells. Neurodegenerative disorders manifest themselves at various levels resulting in very diverse symptoms, including partial or complete loss of motor functions, partial or complete loss of memory, partial or complete loss of speech, partial or complete loss of cognitive skills and behavioral changes, etc. Neurodegenerative disorders include Alzheimer's disease (ALZ), Parkinson's Disease (PD), Huntington's Disease and Amyotrophic lateral sclerosis (ALS).

Of the neurodegenerative disorders, Parkinson's disease (also known as Parkinson's or PD) affects millions of individuals every year. Although its cause remains unknown, PD is associated with the loss or reduction of dopamine-producing neurons. Dopamine is a hormone produced by the brain. It is a chemical messenger that affects the brain processes that control, among other things, movement, emotional response, and the capacity to feel pleasure and pain. The loss or reduction of dopamine is believed to directly or indirectly cause the symptoms of PD.

PD is characterized by muscle rigidity, tremor, postural abnormalities, gait abnormalities, a slowing of physical movement (bradykinesia) or a loss of physical movement (akinesia) in extreme cases. Other symptoms may include gradual loss of cognitive abilities, depression, emotional changes, behavioral changes, loss of speech, and difficulty in swallowing, chewing and sleep disruptions.

Currently there is no cure for PD or other neurodegenerative disorders, since no known treatment can stop or reverse the breakdown of nerve cells. Treatments for PD aim primarily to alleviate PD-induced symptoms. Treatments for treating PD-induced symptoms can be grouped in two main categories: surgical procedures and pharmacological therapies (Table 1).

In severely affected PD patients, as shown in Table 1, surgical procedures, including ablation, deep brain stimulation, pallidotomy and cerebral transplantation, are considered. In ablation, a defined area of the brain deemed affected by Parkinson's is destroyed. In deep brain stimulation, the targeted area is inactivated by implanted electrodes. Pallidotomy is a delicate surgical procedure wherein a fine probe measures abnormal electrical activity of a precise region of the brain, and another probe delivers small electric shocks. The patient, who is awake during the surgery, describes the effects of the electric shocks to pinpoint the area for treatment. The surgeon then burns a tiny hole in the affected cells. Cerebral transplantation implants dopamine-producing cells into the brain. Surgical procedures are invasive, carry inherent risks of infection, stroke or internal bleeding, and have adverse side effects. Furthermore, their effectiveness is uncertain.

For most PD patients, treatment centers on the administration of medications to relieve symptoms. Table 1 lists some common classes of therapies or medications used to treat PD patients. Every patient responds differently to a medication or dosage level, thus treatment needs to be tailored to each individual, taking into consideration various factors such as severity of symptoms, age, and other concurrent medical issues. All medications cause adverse side effects, as further discussed below.

TABLE 1

| SURGICAL TREATMENTS | PHARMACOLOGICAL TREATMENTS |
| --- | --- |
| Ablation | Carbidopa/Levodopa therapy |
| Deep brain stimulation | Dopamine Agonists |
| Pallidotomy | Anticholinergics |
| Cerebral Transplantation | MAO-B Inhibitors |
|  | COMT Inhibitors |
|  | Others |

Of the currently available pharmacological treatments, levodopa is considered the most effective medication for treating PD symptoms. Levodopa is converted into dopamine by an enzyme in the brain. Levodopa does not slow the disease process, but it improves muscle movement and delays severe disability. However, levodopa can cause many side effects, including nausea, vomiting, headache, dizziness, fainting, weakness, decreased blood pressure. In elderly patients, levodopa can cause depression, confusion and visual hallucination. Furthermore, levodopa can become ineffective over time. Increased dosing and prolonged use of levodopa cause additional side effects, such as dyskinesias (spontaneous, involuntary movements) and "on-off" periods when the medication suddenly and unpredictably starts or stops working.

Levodopa is generally used in combination with other medications. Among these, carbidopa prolongs the effect of levodopa by blocking the breakdown of levodopa in the liver, thus increasing the amount of levodopa that reaches the brain. Therefore, a smaller dose of levodopa is needed to treat symptoms. In addition, carbidopa reduces some of the nausea and vomiting associated with levodopa treatment. However, adverse side effects caused by levodopa treatment as discussed above are still prevalent in carbidopa/levodopa therapy.

Referring again to Table 1, another class of pharmacological treatments for PD includes dopamine agonists, which mimic dopamine's function in the brain. Dopamine agonists can be used alone, but they are generally less effective in controlling symptoms. Therefore, they are used primarily as adjuncts to levodopa/carbidopa therapy. Side effects of dopamine agonists include nausea, sleepiness, dizziness, and headache.

Anticholinergics, another class of medications to treat PD, do not act directly on the dopaminergic system but they decrease the activity of acetylcholine, another chemical messenger that controls movement, to balance the diminished dopamine activity. They are also used as adjuncts to levodopa. Adverse effects of anticholinergics include blurred vision, dry mouth and urinary retention. In older patients, they can cause confusion and hallucination.

MAO-B inhibitors, which belong to another class of medications for alleviating PD-induced symptoms, are also used in combination with levodopa. MAO-B inhibitors boost the effects of levodopa by preventing the breakdown of dopamine, thus increasing the amount of available dopamine in the brain. Side effects of MAO-B inhibitors include nausea, dizziness, abdominal pain, confusion, hallucinations and dry mouth.

COMT inhibitors, another class of PD medications, generally must be taken with levodopa. COMT inhibitors prolong symptom relief by blocking the action of an enzyme which breaks down levodopa, allowing a larger amount of levodopa to reach the brain, which raises the dopamine level. Side effects of COMT inhibitors include vivid dreams, visual hallucination, nausea, sleep disturbances, daytime drowsiness, headache and dyskinesia.

It is common for PD patients to take a variety of these medications, all at different doses and at different times of day in order to manage the symptoms of the disease. Variable dosing during a particular day or between days may result in decreased effectiveness of treatment or symptoms management during a day or between days. In addition to the described side effects, prolonged use and increased dosing of the medications render them ineffective over time, or result in "on-off" periods when the medications suddenly and unpredictably start or stop working. Therefore, drug dosage and medication regimens generally are constantly monitored and adjusted to manage the PD symptoms as well as the side effects.

BRIEF SUMMARY OF THE INVENTION

Aspects of the present invention provide for the treatments of neurological disorders. In one aspect of the invention, the invention provides a method of treating neurological disorders in a patient comprising administering a therapeutically effective amount of oxytocin or one or more oxytocin analogs to the patient.

In another aspect of the invention, the invention provides a method of treating one or more symptoms of a neurodegenerative disorder in a patient comprising administering an effective dose of oxytocin or one or more oxytocin analogs to the patient. In some aspects, the neurodegenerative disorder is Parkinson's disease. In some aspects, the method further comprises administering one or more adjunctive therapies. In some aspects, the administering the therapeutically effective amount of oxytocin or the one or more oxytocin analogs is performed simultaneously with, prior to; after, or combinations thereof, the administering the one or more adjunctive therapies.

In another aspect of the invention, the invention provides a method for alleviating one or more symptom of Parkinson's disease in a patient, the method comprising administering adjunctive therapies and administering a therapeutically effective amount of oxytocin or one or more oxytocin analogs to the patient. In some aspects, the invention provides for administration of the therapeutically effective amount of oxytocin or one or more oxytocin analogs to the patient between administrations of the adjunctive therapies. In some aspects, the invention provides for administration of the therapeutically effective amount of oxytocin or one or more oxytocin analogs in a last half of a time period bounded by administration of the same adjunctive therapy.

In another aspect of the invention, the invention provides a method of determining the effectiveness of oxytocin therapy for alleviating one or more symptoms of Parkinson's disease in a patient, the method comprising: generating a first profile wherein the patient's one or more symptoms is quantifiably evaluated; administering an effective amount of oxytoxin or one or more oxytocin analogs to the patient; generating a second profile wherein the patient's one or more symptoms is quantifiably re-evaluated; and comparing the first profile and the second profile to determine whether the difference is significant. In another aspect, the administering the effective amount is performed in one or more doses.

In yet another aspect of the invention, the invention provides a method of determining the effectiveness of oxytocin therapy in enhancing one or more adjunctive therapies for alleviating one or more symptoms of Parkinson's disease in a patient, the method comprising: suspending the patient form the one or more adjunctive therapies; generating a referenced profile wherein the patient's one or more symptoms is quantifiably evaluated; administering to the patient the one or more adjunctive therapies; generating a first treatment profile wherein the patient's one or more symptoms is quantifiably evaluated; administering an effective amount of oxytoxin or one or more oxytocin analogs to the patient; generating a second treatment profile wherein the patient's one or more symptoms is quantifiably re-evaluated; and comparing the referenced profile, the first treatment profile and the second treatment profile.

These and other aspects of the invention are more fully comprehended on review of this disclosure.

DETAILED DESCRIPTION

The present disclosure provides methods of treating neurodegenerative disorders including Parkinson's disease (PD). In various embodiments, the present methods use oxytocin or one or more oxytocin analogs to treat neurodegenerative disorders. In other embodiments, the present methods use oxytocin or one or more oxytocin analogs to alleviate one or more symptoms of PD in a patient. In some embodiments, the present methods use oxytocin therapy in conjunction with one or more adjunctive therapies to alleviate one or more symptoms of PD.

As used herein, the term "analog" refers to any molecule that demonstrates activity similar to that of the parent molecule. Such a molecule may be a synthetic analog, fragment, derivative pharmaceutically acceptable salt or endogenous biological molecule capable of similar activity to the parent compound.

As used herein, the term "oxytocin analog" refers to any naturally occurring or synthetic molecules which exhibit oxytocin activity but which may have a different potency or pharmacological profile.

As used herein, the term "therapeutically effective amount" "an effective dose" refers to an amount of the compound which, depending on the selected mode, frequency and duration of administration, produces a desired effect.

As used herein, the term "oxytocin therapy" refers to the administration of a therapeutically effective amount of oxytocin or one or more oxytocin analogs or a pharmaceutical composition containing a therapeutically effective amount of oxytocin or oxytocin analogs to a patient to produce a desired effect.

Figure 1:
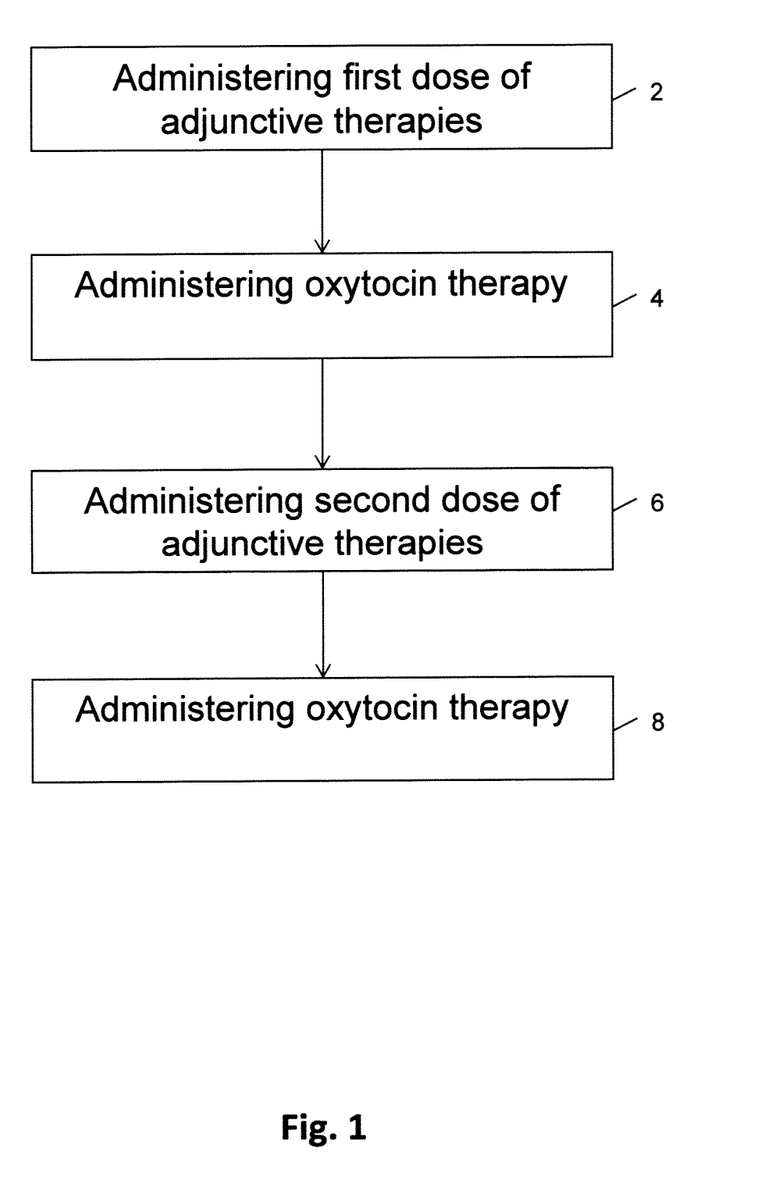
FIG. 1 is a flowchart for a method of using oxytocin therapy in conjunction with adjunctive therapies to alleviate one or more symptoms of PD in a patient.

FIG. 1 is a flow chart of a method of using oxytocin therapy in conjunction with adjunctive therapies to alleviate one or more PD symptoms in a patient, although it should be recognized that the terminology may be reversed as to what is considered "adjunctive therapy". In some embodiments, oxytocin therapy is administered along with adjunctive therapies, which may include treatments or drugs, useful for alleviating PD-induced symptoms, including but not limited to therapies comprising levodopa and carbidopa, dopamine agonists, anticholinergics, MAO-B inhibitors, COMT inhibitors or combinations thereof.

In some embodiments, oxytocin therapy is administered simultaneously with one or more adjunctive therapies. In alternative embodiments, oxytocin therapy is administered prior to administrations of one or more adjunctive therapies. In another embodiment, oxytocin therapy is administered after administrations of one or more adjunctive therapies. In one specific embodiment, oxytocin therapy is administered between consecutive administrations of one or more adjunctive therapies. In some embodiments, the adjunctive therapies comprise carbidopa/levodopa therapy, dopamine agonists, anticholinergics, MAO-B inhibitors, COMT inhibitors or combinations thereof. In some embodiments, oxytocin therapy is administered between a time period between consecutive administrations of a same adjunctive therapy. In some embodiments, oxytocin therapy is administered during a first half of a time period bounded by administrations of the same adjunctive therapy. In other embodiments, oxytocin therapy is administered during a last half of the time period. In other embodiments, oxytocin therapy is provided during a last fourth of the time period.

With reference to FIG. 1, in block 2, the method includes administering to the patient a first dose of the adjunctive therapies. In some embodiment, the adjunctive therapies include levodopa/carbidopa therapy. In block 4, the method comprises administering oxytocin therapy to the patient. In some embodiments, administering oxytocin therapy includes administering a therapeutically effective amount of oxytocin or oxytocin analogs to the patient.

Oxytocin therapy may be administered via various administration routes, as further discussed below. In some embodiments, oxytocin therapy is administered intranasally. In one specific embodiment, oxytocin therapy is administered by way of an inhaler, such as those used in nasal sprays.

In some embodiments, the therapeutically effective amount of oxytocin or oxytocin analogs administered ranges from 10 IU to 150 IU. In one specific embodiment, 40 IU of oxytocin is administered intranasally to the patient. In some embodiments, administering oxytocin therapy comprises administering the therapeutically effective amount of oxytocin or oxytocin analogs in multiple doses. In one embodiment, a unit dose of 5 IU oxytocin is administered into the left nostril of the patient. Subsequently, another unit dose of 5 IU oxytocin is administered into the right nostril of the patient. The process is repeated until a total of 40 IU oxytocin is administered to the patient. In other embodiments, the administering block 4 may be performed orally, intravenously or transdermally. Depending on the route of administration, oxytocin or oxytocin analogs may be administered as a pharmaceutical composition including one or more acceptable carriers, as further discussed below.

The oxytocin therapy administered in block 4 can be performed simultaneously with or after administering the first dose of the adjunctive therapies in block 2. In some embodiments, oxytocin therapy is administered from one to three hours after administration of the adjunctive therapies. In other embodiments, oxytocin therapy is administered from 5 minutes up to 1 hour after administration of the adjunctive therapies. In some other embodiments, oxytocin therapy is administered more than 3 hours after administration of the adjunctive therapies. In alternative embodiments, oxytocin therapy is administered before administration of the adjunctive therapies.

In block 6, the method comprises administering a second dose of the adjunctive therapies. In block 8, administration of oxytocin therapy is optimally repeated. The method may comprise additional administrations of the adjunctive therapies, such as a third dose and fourth dose of the adjunctive therapies. In some embodiments, administering the adjunctive therapies and administering oxytocin therapy are iteratively repeated over an extended period of time.

In some embodiments, administering oxytocin therapy is performed in a time period between administering the first dose of the adjunctive therapies in block 2 and administering the second dose of the adjunctive therapies in block 6. In some embodiments, oxytocin therapy is administered during a first half of the time period between the administering of the first dose in block 2 and the administering of the second dose in block 6. In other embodiments, oxytocin therapy is administered during a last half of the time period. In other embodiments, oxytocin therapy is provided during a last fourth of the time period.

In some embodiments including the illustrated embodiment, oxytocin therapy is administered between consecutive administrations of the adjunctive therapies. In alternative embodiments, oxytocin therapy is administered between every other administration of the adjunctive therapies. In yet other embodiments, oxytocin therapy is administered only after a first dose of the adjunctive therapies. In yet other embodiments, oxytocin therapy is administered only after a last dose of the adjunctive therapies. In another embodiment, oxytocin therapy is administered only after a second or third dose of the adjunctive therapies.

Figure 2:
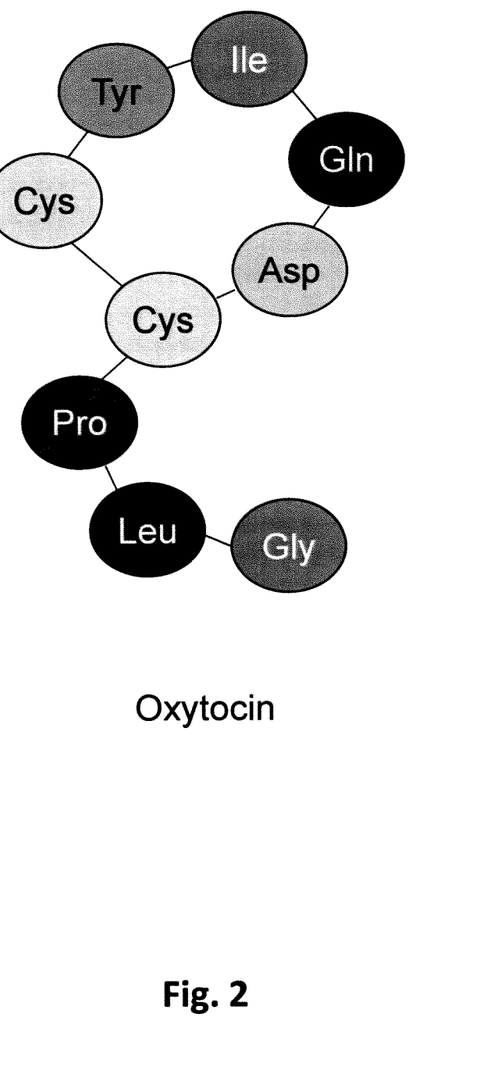
FIG. 2 shows the structure of oxytocin.

Oxytocin for use in the methods herein can be natural or synthetic. FIG. 2 shows the structure of oxytocin, a nine amino acid cyclic peptide hormone. Endogenous or natural oxytocin is a short-lived, fast acting hormone made by the hypothalamus of the brain. Oxytocin is currently prepared synthetically and sold under various trade names including Pitocin (Parke-Davis, Morris Plains, N. J.) and Syntocinon. Oxytocin is approved by the Food and Drug Administration for intravenous use to induce labor in pregnant women as well as for the treatment of postpartum hemorrhage. Oxytocin is also used to facilitate the release of milk from the breast during nursing. Studies have shown that oxytocin may exert a wide spectrum of other biological effects including control of memory and learning process, and various types of maternal and sexual behavior. In addition, oxytocin may participate in the control of cardiovascular functions, thermoregulation and fluid balance.

Oxytocin analogs suitable for the present methods may include, but are not limited to, 4-threonine-1-hydroxy-deaminooxytocin, 4-serine,8-isoleucine-oxytocin, 9-deamidooxytocin, 7-D-proline-oxytocin and its deamino analog, (2,4-diisoleucine)-oxytocin, deamino oxytocin analog, 1-deamino-1-monocarba-E12-Tyr(OMe)]-OT(dCOMOT), carbetocin, 4-threonine, 7-glycine-oxytocin (TG-OT), oxypressin, deamino-6-carba-oxytoxin (dC60), L-371,257 and the related series of compounds containing an ortho-trigluoro-ethoxyphenylacetyl core such as L-374,943.

In some embodiments, oxytocin or oxytocin analogs may be administered as a pharmaceutical or pharmacological composition. The pharmaceutical or pharmacological composition includes a therapeutically effective amount of oxytocin or one or more oxytocin analogs and one or more pharmaceutically acceptable carriers.

As used herein, "pharmaceutically acceptable carrier" refers to any agents which do not cause an intolerable side effect and which allow oxytocin to retain its pharmacological activity in the body. A pharmaceutically acceptable carrier includes excipients, emulsifiers, solubilizers, surfactants, buffers, preservatives, and/or other additives which may enhance stability, delivery, absorption, half-life, efficacy, pharmacokinetics, pharmacodynamics, reduce adverse side effect or provide other advantages for pharmaceutical use.

Suitable pharmaceutically acceptable carriers will be apparent to those skilled in the art of pharmaceutical formulations. Exemplary pharmaceutically acceptable carriers include, but are not limited to, mannitol, urea, dextrans, lactose, potato and maize starches, magnesium stearate, talc, vegetable oils, polyalkylene glycols, ethyl cellulose, poly(vinylpyrrolidone), calcium carbonate, chitosan, ethyl oleate, isopropyl myristate, benzyl benzoate, sodium carbonate, gelatin, potassium carbonate, silicic acid, phosphatidylcholine, phosphatidylserine, and sphingomyelins, edetate disodium (EDTA), polysorbate and other conventionally employed acceptable carriers.

The choice of a suitable pharmaceutically acceptable carrier will depend on the exact nature of the particular formulation desired, e.g., whether oxytocin or oxytocin analogs is to be formulated into a liquid solution, a suspension, an ointment, a film or a gel. The choice of a suitable pharmaceutically acceptable carrier will also depend on the route of administration. Preferably, the carrier is formulated to be suitable for a chosen route of administration.

Oxytocin or oxytocin analogs according to the present methods may be administered via oral, intravenous, intranasal, intrapulmonary, subcutaneous, transcumosal or transdermal administration. In some embodiments, oxytocin or oxytocin analogs are administered intranasally.

In some embodiments, oxytocin or oxytocin analogs is formulated in a pharmaceutical carrier suitable for intranasal administration. Intranasal formulations are provided as aqueous solutions or suspensions or powders for intranasal delivery as an aerosol to facilitate administration and enhance delivery. In alternative embodiments, oxytocin or oxytocin analogs is formulated in a pharmaceutical carrier suitable for intravenous, intramuscular, subcutaneous, oral or transdermal administration. Formulations suitable for a desired route of administration are within the skill of one in the art.

Nasal or intranasal drug delivery can be carried out using devices including, but not limited to, unit dose containers, pump sprays, droppers, squeeze bottles, airless and preservative-free sprays, nebulizers (devices used to change liquid medication to an aerosol particulate form), metered dose inhalers, and pressurized metered dose inhalers. Nasal or intranasal drug delivery systems are known in the art and several are commercially available.

Oxytocin or oxytocin analogs suitable for the present methods is administered in a therapeutically effective amount, according to the intended use and the desired results. For example, a therapeutically effective amount can be an amount sufficient to alleviate one or more symptoms in a PD patient. The therapeutically effective amount can be determined empirically and depends on a number of factors, including but not limited to the severity of the PD-induced symptoms, the route of administration, the size, weight, age and overall health of the patient. Such determinations are within the skill of one in the art.

Non-limiting examples of suitable therapeutically effective amounts of oxytocin or oxytocin analogs range from about 0.1 IU to about 500 IU, 1 IU to 400 IU, 5 IU to 200 IU, 10 IU to 100 IU, or 15 IU to 50 IU.

The therapeutically effective amount of oxytocin or oxytocin analogs suitable for the present methods may be administered in a single or multiple unit doses. For example, one or more unit doses may be administered two, three, four, up to ten times daily. The amount of oxytocin or oxytocin analogs administered as a unit dose will also depend upon the type of pharmaceutical composition being administered, for example, a solution, a suspension, an emulsion, a powder, or a sustained-release formulation. Such determinations are within the skill of one in the art.

Aspects of the present invention provide a method for determining the effectiveness of oxytocin therapy for alleviating PD-induced symptoms in a patient.

Figure 3:
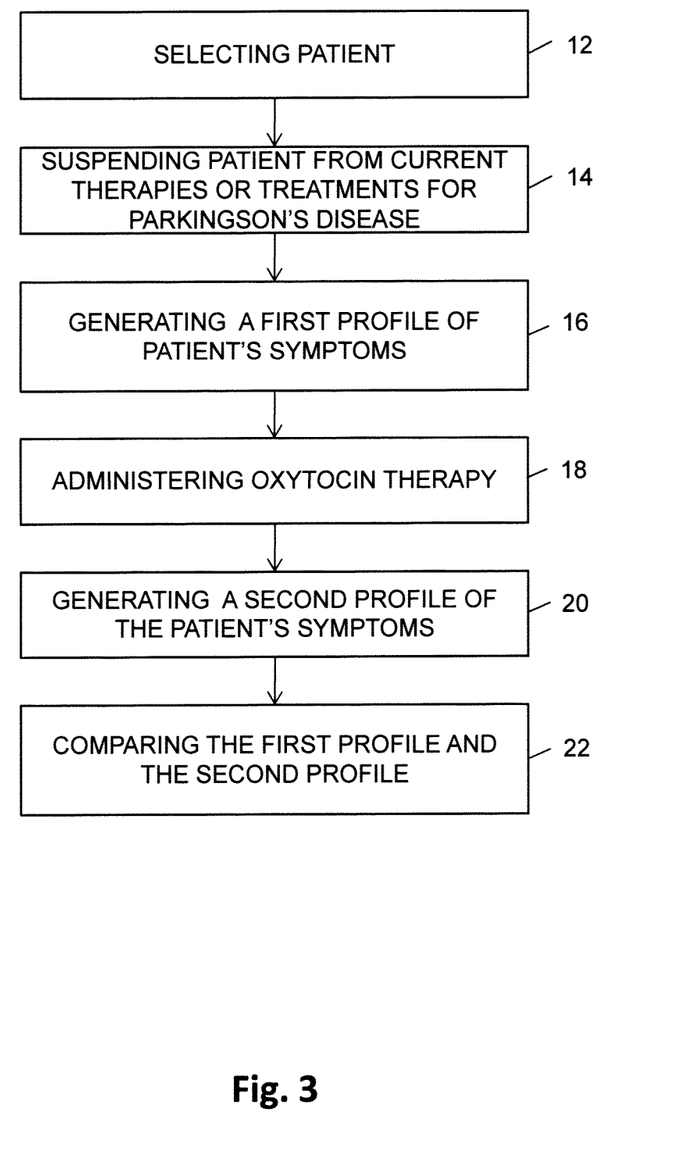
FIG. 3 is flowchart for a method of determining the effectiveness of an oxytocin therapy in accordance with aspects of the invention.

FIG. 3 is a flow chart of a method for determining the effectiveness of oxytocin therapy in alleviating one or more PD-induced symptoms in a patient. The method includes selecting a patient eligible for oxytocin therapy in block 12. Selecting the patient in block 12 may comprise screening patients with a confirmed diagnosis for a neurodegenerative disorder such as PD. In some embodiments, only patients exhibiting tangible or observable symptoms that are characteristics of the neurological disorder of interest, such as for instance some loss of motor functions or cognitive skills are selected. In some embodiments, to test the efficiency of oxytocin therapy on different stages of the disorder, patients with very severe manifestation of the disorder are selected. In alternative embodiments, patients with mild symptoms are selected. In yet another embodiment, patients exhibiting various levels of symptoms are selected.

In some embodiments, patients having concurrent medical conditions, such as heart conditions, liver or kidney problems, a history of strokes or other serious medical conditions are excluded. Furthermore, as oxytocin is known to induce smooth muscle contraction and consequently induce labor, pregnant patients are typically excluded. In some embodiments, only male patients are considered for oxytocin therapy. In alternative embodiments, wherein participants include both male and female patients, only female patients who are either post-menopausal or utilizing at least two forms of contraception are selected. As female patients who are pre-menopausal may exhibit small variations of oxytocin levels during their menstrual cycle, in some embodiments, only post-menopausal patients are selected.

Once a patient has been selected, in block 14, the method comprises temporarily suspending the patient from current treatments or therapies for alleviating PD-induced symptoms. Without the treatments or therapies to manage PD-induced symptoms, the patient generally experiences a return or an enhancement of their PD symptoms. In some embodiments, the patient is asked to discontinue any treatments or therapies for alleviating PD-induced symptoms for a period ranging from a day to several weeks prior to administration of oxytocin therapy. In some embodiments, the patient is taken off any current therapies or treatments for a day to a week. In one embodiment, the patient is asked to discontinue his or her current therapies or treatments for at least a day prior to oxytocin therapy.

In block 16, the method comprises generating a first profile of the patient's symptoms, wherein among other things, the severity of the patient's one or more PD-induced symptoms is quantifiably assessed. As set forth above, typical PD-induced symptoms comprise muscle rigidity, tremor, partial or complete loss of motor skills, partial or complete loss of cognitive abilities, partial or complete loss of speech, emotional changes, behavioral changes or combinations thereof. In some embodiments, generating the first profile comprises quantifiably evaluating the severity of the patient's PD-induced symptoms according to standardized protocols. In some embodiments, generating the first profile comprises quantifiably assessing, among other PD-induced symptoms, the patient's motor skills, cognitive skills, emotional status, or combinations thereof. In some embodiments, generating the first profile comprises quantifiably assessing the patient's motor skills. In other embodiments, generating the first profile comprises quantifiably assessing the patient's motor skills and cognitive skills. In yet other embodiments, generating the first profile measurably evaluates the patient's motor skills and emotional status. In other embodiments, generating the first profile comprises generating a comprehensive report including but not limited to the patient's mental status, motor skills, cognitive skills, emotional status and combinations thereof.

In some embodiments, generating the first profile comprises utilizing the Unified Parkinson's Disease Rating Scale (or UPDRS) to quantifiably evaluate the patient's motor skills. The UPDRS is a battery of tests designed to assess Parkinsonian symptoms, including Mentation, Behavior and Mood, Activities of Daily Living, and Motor sections. An example of the UPDRS is provided in Appendix 1.

In some embodiments, the Motor section of the UPDRS is used to rank the extent of the patient's motor deficiencies. The Motor section of the UPDRS comprises an examination of speech, facial expression, tremor at rest in each of the extremities, posture and postural tremors, rigidity, hand movements, gait, arising from a chair, and bradykinesias (slow movement) or hypokinesias (diminished muscle movement). In one specific embodiment, the motor skills of the patients are rated on a scale of zero to four, with four being the symptom at its most severe state.

In some embodiments, generating the first profile further comprises quantifiably evaluating the patient's cognitive skills by using a standardized cognitive test including a basic personal information questionnaire and a number of working memory tasks to assess mental status.

In other embodiments, generating the first profile further comprises quantifiably evaluating the patient's emotional status. In some embodiments, the patient is given a series of questions designed to assess the patient's emotional status, specifically their levels of trust, anxiety, attachment and/or avoidance, and affect intensity measure.

In block 18, the method comprises administering oxytocin therapy to the patient. The oxytocin therapy administered in block 18 may be performed via any of the administration routes discussed above. In some embodiments, the oxytocin therapy is performed intranasally. In one specific embodiment, the oxytocin therapy is administered by way of an inhaler, such as those used in nasal sprays. In some embodiments, administering oxytocin therapy includes administering a therapeutically effective amount of oxytocin or oxytocin analogs. In some embodiments, the therapeutically effective amount of oxytocin or oxytocin analogs administered ranges from 10 IU to 150 IU. In one specific embodiment, 40 IU of oxytocin is administered intranasally to the patient. In some embodiments, the administering block 4 comprises administering the therapeutically effective amount of oxytocin or oxytocin analogs in multiple doses. In one embodiment, a unit dose of 5 IU oxytocin is administered into the left nostril of the patient followed by administration of another unit dose of 5 IU oxytocin into the right nostril of the patient. The process is repeated until a total of 40 IU oxytocin is administered to the patient. In other embodiments, the administering block 18 may be performed orally, intravenously or transdermally.

Subsequent to oxytocin therapy administration, the method comprises generating a second profile in block 20. As it takes time for the administered oxytocin or oxytocin analog to reach a high enough concentration in the brain to have an effect, the method allows a lapse time between administering oxytocin therapy and generating the second profile. The lapse time may vary depending, among other things, on the route of administration or the amount of oxytocin or oxytocin analogs administered, the nature of the pharmaceutical composition (e.g. liquid, spray, gel or ointment) or combinations thereof. In some embodiments, the lapse time ranges from 5 minutes to 3 hours. In some embodiments, the lapse time ranges from 30 minutes to 1 hour. To shorten the required lapse time, in some embodiments, oxytocin therapy is administered simultaneously, shortly before or shortly after generating the first profile in block 16.

Generating the second profile comprises quantifiably evaluating the severity of the patient's PD symptoms subsequent to oxytocin therapy administration. In some embodiments, generating the second profile comprises quantifiably assessing the patient's motor skills, cognitive skills, emotional status or combination thereof. In some embodiments, generating the second profile comprises quantifiably evaluating the same PD-induced symptoms as the ones assessed in generating the first profile in block 16. In some embodiments, generating the second profile comprises utilizing the same standardized protocols which were used in the generating the first profile in block 16. Thus, in some embodiments, the USPDR is used to quantifiably evaluate the patient's motor skills.

To determine the effectiveness of oxytocin therapy in alleviating PD-induced symptoms in the patient, the method further comprises comparing the first profile and the second profile in block 22 as within the skill of one in the art.

According to the methods provided herein, the efficacy of oxytocin therapy in alleviating PD-induced symptoms can also be quantifiably assessed in a group of patients. For instance, a sample of patients, of any size, can be selected and the patients within the sample are individually tested according to aspects of the present methods. The response of all the selected patients to oxytocin therapy can be analyzed to quantifiably evaluate the efficacy of the tested therapy.

Figure 4:
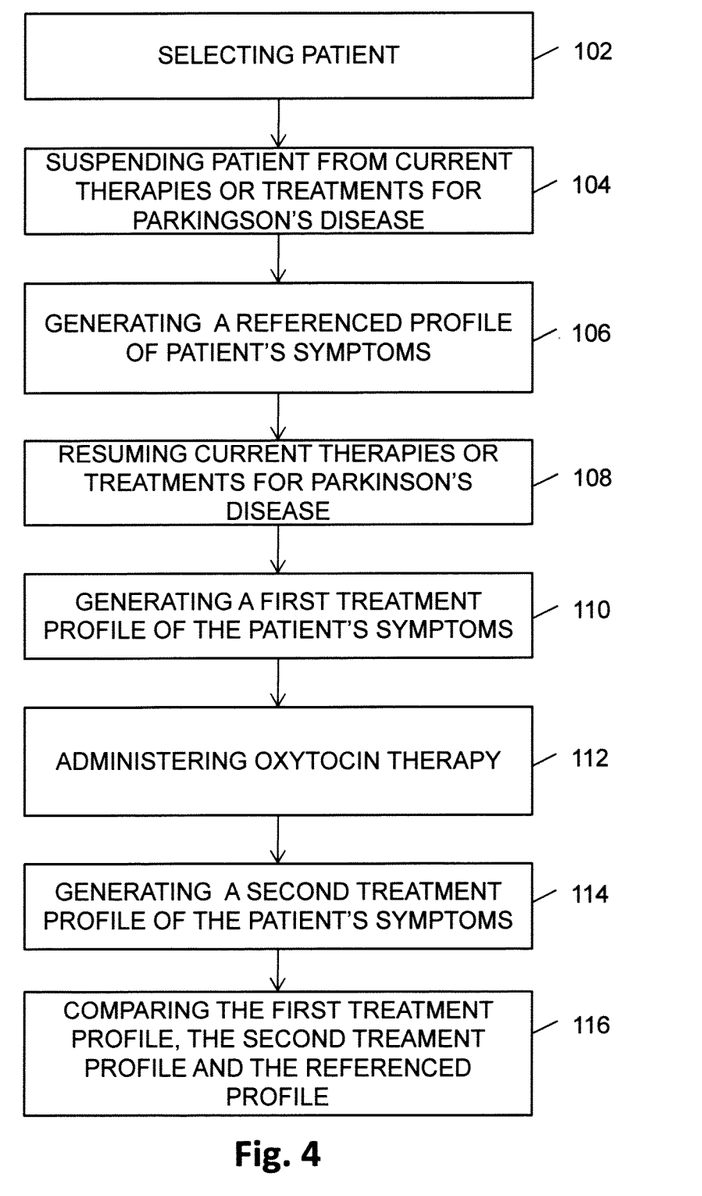
FIG. 4 is a flowchart for a method of determining the effectiveness of an oxytocin therapy in complementing alternative PD-alleviating treatments.

FIG. 4 is a flow chart of a method for determining the effectiveness of oxytocin therapy in complementing the therapeutic effect of adjunctive therapies for alleviating PD-induced symptoms.

The method comprises selecting a patient exhibiting PD-induced symptoms in block 102. Similarly to the method described with reference to FIG. 3, in some embodiments, selecting the patient comprises selecting a patient based on a confirmed diagnosis for a neurodegenerative disorder of interest, such as PD. In some embodiments, selecting the patient comprises identifying patients exhibiting tangible or observable symptoms of PD, such as for instance some loss of motor functions or cognitive skills. In some embodiments, selecting the patient comprises excluding patients having concurrent serious medical problems or pregnant. In some embodiments, the method comprises selecting only male patients and/or post-menopausal female patients.

Once a patient has been selected, the method comprises temporarily suspending the patient from current adjunctive therapies or medications for alleviating PD-induced symptoms in block 104. The "off" period, wherein the patient discontinues his or her current medications or therapies, can vary from a day to several weeks. In some embodiments, the patient is asked to discontinue all PD therapies or medications for at least one day to three days. In some embodiments, the "off" period simply means the time between regular doses of medications. Without the medications, the patient generally experiences a return or an enhancement of their PD symptoms.

The method further comprises generating a referenced profile for the patient in block 106. The referenced profile measurably evaluates the severity of the patient's PD-induced symptoms in the absence of any medications, therapies or treatments. In some embodiment, the referenced profile is generated by measurably evaluating, among other things, the patient's motor skills, cognitive skills, emotional status, mental status or combinations thereof according to standardized protocols. In some embodiments, the standardized protocol utilized comprises the Unified Parkinson's Disease Rating Scale (or UPDRS). In some embodiments, alternative standardized protocols are used to measurably evaluate the motor skills, cognitive skills, emotional status or combinations thereof of the patient. In other embodiments, the patient's motor skills, cognitive skills and emotional status can be evaluated by alternative methods.

In some embodiments, generating the referenced profile in block 106 comprises measurably evaluating the patient's PD-induced symptoms, such as motor skills, cognitive skills, emotion status, mental status or combinations thereof, at various time intervals. In some embodiments, generating the referenced profile comprises measurably assessing the patient's PD-induced symptoms according to a schedule that the patient's adjunctive therapies or treatments are routinely administered. For instance, if the patient normally takes his or her PD medications three times a day, in the morning, afternoon, and evening, the referenced profile includes reports measurably assessing the patient's PD-induced symptoms in the morning, afternoon and evening. The referenced profile generated in block 106 serves as a baseline against which the effectiveness of current, new therapies or combinations thereof is determined.

The method comprises resuming the patient's adjunctive therapies or medications for alleviating PD-induced symptoms at block 108. Subsequently, the method includes generating a first treatment profile of the patient at block 110, wherein the severity of the patient's PD induced symptoms is quantifiably assessed. In some embodiments, generating the first treatment profile comprises quantifiably assessing the patient's PD-induced symptoms using the same standardized protocols as the ones used in generating the referenced profile. To ensure that a change in PD-induced symptoms are attributable to the medications or therapies, as it may take time for medications to reach steady state or constant concentrations in the brain, in some embodiments, a minimum lapse time ranging from at least one day to several days is allocated between resuming the current therapies in block 108 and generating the first treatment profile in block 110. In some embodiments, the minimum lapse time is 3 days. In some embodiments, the minimum lapse time is a week. In some other embodiments, the minimum lapse time is more than a week. In one specific embodiment, a lapse time of 1 day is provided between resuming the current therapies and generating the first treatment profile. In some embodiments, the minimum lapse is simply the time period between regular doses of the medications or therapies.

In some embodiments, generating the first treatment profile comprises quantifiably assessing the patient's PD-induced symptoms at different time intervals. In some embodiments, generating the first treatment profile comprises quantifiably evaluating the patient's PD-induced symptoms according to a schedule whereby adjunctive medications or therapies for alleviating PD-symptoms are administered. In one embodiment, generating the first treatment profile comprises measurably assessing the patient's symptoms between administrations of adjunctive therapies or medications. For instance, if the patient takes his or her medications three times a day, such as in the morning, afternoon and evening, generating the first treatment profile may comprise quantifiably assessing the patient's PD-induced symptoms shortly before or after the patient takes his or her medications. Compared to the referenced profile generated in block 106, the first treatment profile generated in block 110 shows the therapeutic effects of the adjunctive therapies or medications in alleviating the patient's PD-induced symptoms. Comparison of the referenced profile and the first treatment profile at different time intervals minimizes unwanted confounding factors and ensures that the observed effects are primarily attributable to the adjunctive therapies or medications administered. Such comparison is also useful for identifying "off" period, wherein the administered therapies or medications are not effective or less effective in alleviating PD-induced symptoms.

The method further comprises administering oxytocin therapy to the patient in block 112. In some embodiments, administering oxytocin therapy comprises administering a therapeutically effective amount of oxytocin or oxytocin analogs. In some embodiments, oxytocin therapy is administered intranasally. In some embodiments, oxytocin therapy is administered at different time intervals. In some embodiments, oxytocin therapy is administered according to a schedule whereby other concurrent adjunctive therapies or medications for alleviating PD-induced symptoms are administered. In some embodiments, oxytocin therapy is administered between administrations of other concurrent adjunctive therapies. In some embodiments, the method comprises administrating oxytocin therapy at various doses or concentrations. In some embodiments, oxytocin therapy is administered at various times intervals at various doses or combinations thereof. In some embodiments, oxytocin therapy is administered intravenously, orally or transdermally.

As it takes time for the administered oxytocin or oxytocin analogs to reach a high enough concentration in the brain to have an effect, the method allows a lapse time after oxytocin therapy is administered before generating a second treatment profile in block 114. The lapse time between administering oxytocin therapy in block 112 and generating the second treatment profile in block 114 can range from 30 minutes to 3 hours. In some embodiments, the lapse time ranges from 45 minutes to 2 hours. In one specific embodiment, a lapse time of 1 hour is provided between administrating oxytocin therapy in block 112 and generating the second treatment profile in block 114. The second treatment profile generated in block 114 quantifiably assesses the patient's PD-induced symptoms under oxytocin therapy in conjunction with the patient's concurrent adjunctive therapies. In some embodiments, generating the second treatment profile comprises quantifiably evaluating the patient's PD induced symptoms at different time intervals. In some embodiments, generating the second treatment profile comprises quantifiably evaluating the patient's PD induced symptoms before, after or in between different administrations of oxytocin therapies. In some embodiments, generating the second treatment profile comprises quantifiably evaluating the patient's PD induced symptoms at various doses or concentrations of oxytocin therapy.

The method further comprises comparing the second treatment profile, the first treatment profile, the referenced profile or combinations thereof in block 116. In some embodiments, the method compares the first treatment profile with the referenced profile. In other embodiments, the method compares the first treatment profile with the second treatment profile. In yet other embodiments, the method compares the first treatment profile, the second treatment profile and the referenced profile. In some embodiments, the method compares the second treatment profile, the first treatment profile, the referenced profile or combinations thereof is performed at different time intervals. In some embodiments, the method comprises comparing the second treatment profile, the first treatment profile, the referenced profile or combinations thereof at different oxytocin concentrations.

Thus, the method described with reference to FIG. 4 determines whether oxytocin therapy is effective in synergistically enhancing the therapeutic effects of alternative concurrent therapies for alleviating PD-induced symptoms. The described method also allows for the determination of an oxytocin therapy regimen which would best complement or enhance the therapeutic effects of alternative concurrent therapies. Among other things, for instance by comparing the first treatment profile with the referenced profile at different time intervals, the present method identifies "off" periods, wherein the adjunctive therapies are not effective or less effective in alleviating PD-induced symptoms. By comparing the first treatment profile, the second treatment profile and the referenced profile at different time intervals, the present method identifies an optimal schedule wherein oxytocin therapy can be administered to compensate the reduced activity of adjunctive therapies during their "off" period.

Furthermore, in accordance with the methods provided herein, the efficacy of oxytocin therapy in enhancing adjunctive therapies in alleviating PD-induced symptoms can be quantifiably assessed in a group of patients. The information derived from such assessment allows one skilled in the art to determine whether oxytocin therapy is effective as a complementary treatment to adjunctive therapies to alleviate PD-induced symptoms in PD patients.

The following examples are presented to set forth more clearly the subject matter of this disclosure without imposing any limits on the scope thereof. In the examples, the effectiveness of an oxytocin therapy is evaluated by quantifying the motor skills of participating patients before and after oxytocin administration.

In three independent experiments, three male patients exhibiting PD-induced symptoms were selected for oxytocin therapy. The participants were in their "off" period, wherein they were taken off their current medications prior to oxytocin therapy. During the experiment, each participant was given 40 IU (40 ml) of intranasal oxytocin. The synthetic form of oxytocin was administered by way of an inhaler, such as those used in nasal spray decongestants. Five pumps of the inhaler were dispensed into the left nostril of the participants; the participants were asked to inhale deeply through the nose. Five more pumps were dispensed into the right nostril of the participants and again the participants were asked to inhale deeply. This process was repeated so that, in total, the participants received forty pumps of the inhaler, twenty per nostril.

Immediately following oxytocin infusion, the participants were given a battery of physical and cognitive tests, lasting about fifteen to twenty minutes. These tests included the Motor portion of the Unified Parkinson's Disease Rating Scale (UPDRS) as well as a cognitive test used to establish the mental and emotional status of the participants. For each test, the participants were rated on a scale of zero to four, with four being the symptoms at its most severe state. Thus, a reduction in the UPDRS test score corresponds to a reduction in the severity of the exhibited symptoms.

After administration of oxytocin, the participants were asked to wait for 45 minutes to one hour, wherein they passed the time by reading, conversing or simply relaxing. Subsequently, the motor skills of the participants were assessed again using the UPDRS. The administration of the UPDRS the first time was to quantifiably evaluate the patient's symptoms uninfluenced by oxytocin infusion, whereas the second administration of the UPDRS test served to quantifiably assess the motor condition of the patient under the influence of oxytocin.

The participants remained under direct supervision throughout the experiment to ensure their comfort and well-being. Once the experimental procedure was completed, the participants were able to leave the clinic and were asked to continue taking their normal medications. The participants were not in any way restricted in their activities for the rest of the day. In each of the individuals, there were not any lasting effects apparent due to the administration of oxytocin or to the delay of administering their normal medications.

Figure 5:
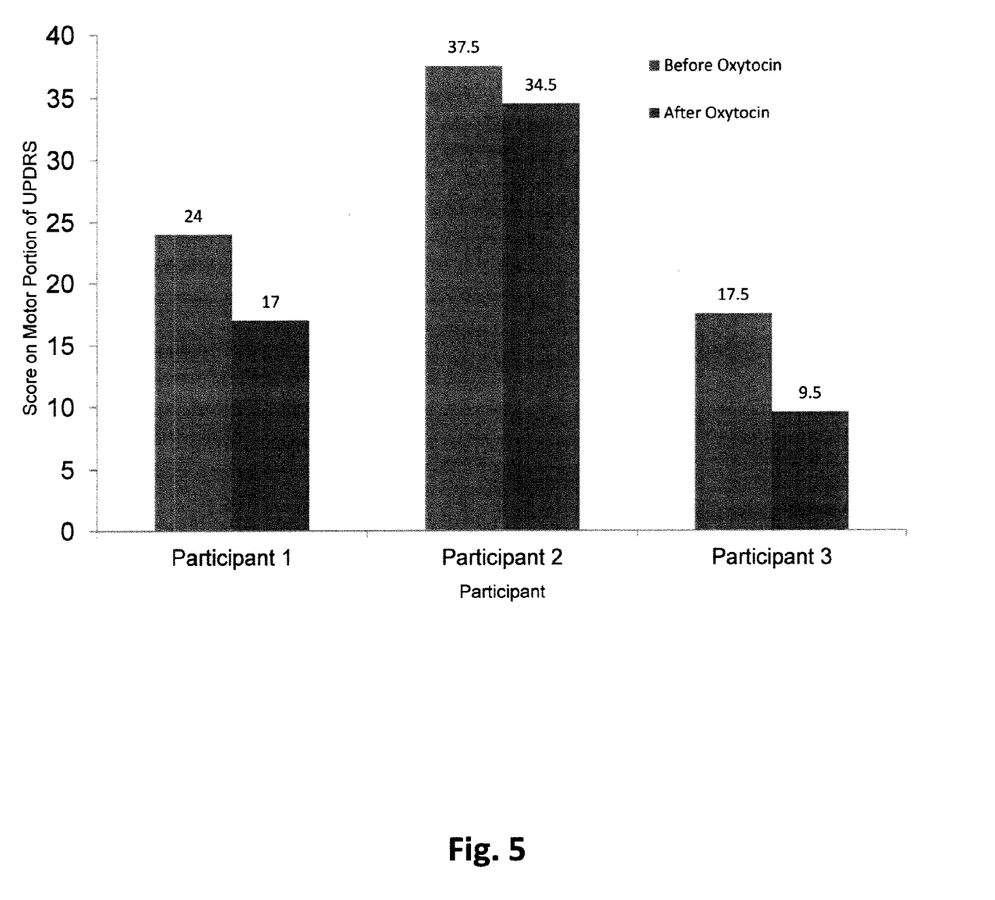
FIG. 5 is a graph summarizing the performance profiles of representative subjects before and after oxytocin therapy.

FIG. 5 illustrates a graph summarizing the performance profiles of the three representative participants before and after oxytocin therapy according to aspects of the present invention. As shown in FIG. 5, participant 1 had an initial total score of 24, which was reduced to 17 after oxytocin therapy, corresponding to a 30% decrease. Participant 2 had an initial total score of 37.5 which was reduced to 34.5 after oxytocin therapy, corresponding to an 8% decrease. Participant 3 had an initial total score of 17.5 which was reduced to 9.5 after oxytocin therapy, corresponding to a 50% decrease. Thus, the effectiveness of the administered oxytocin therapy is participant-dependent.

Accordingly, aspects of the invention provide for methods of treating neurodegenerative disorders, including Parkinson's diseases. Another aspect of the invention provides for methods of alleviating one or more symptoms of one or more PD-induced symptoms. A further aspect of the invention includes a method for determining the effectiveness of oxytocin therapy in alleviating one or more symptoms of PD in a patient. A further aspect of the invention includes a method for determining the effectiveness of oxytocin in complementing alternative concurrent therapies for PD. Although the invention has been described with respect to certain embodiments, it should be recognized that the invention comprises the novel and not obvious claims supported by this disclosure and their insubstantial variations.

The invention claimed is:

1. A method of treating one or more symptoms of Parkinson's disease in a patient, comprising:
   consecutively administering one or more adjunctive therapies to the patient, with a time period between consecutive administrations of the one or more adjunctive therapies; and
   intranasally administering an effective amount of oxytocin to the patient during a last fourth of the time period between the administering a first dose of the one or more adjunctive therapies and a consecutive dose of the one or more adjunctive therapies.

2. The method of claim 1, wherein the therapeutically effective amount is from about 0.1 IU to about 200 IU.

3. The method of claim 1, wherein oxytocin is administered as a pharmaceutical composition.

4. The method of claim 1, wherein the symptoms include at least one of at least some loss of motor functions, loss of cognitive abilities, anxiety, social withdrawal, depression and loss of speech.

5. The method of claim 1, wherein the administering the one or more adjunctive therapies is performed in one or more doses.

\* \* \* \* \*